United States Patent [19]
Gründl et al.

[11] Patent Number: 5,586,968
[45] Date of Patent: Dec. 24, 1996

[54] METHOD AND APPARATUS FOR MOVING AN ENDOSCOPE ALONG A CANAL-SHAPED CAVITY

[76] Inventors: Andreas Gründl, Haseneystrasse 20, D-81377 München; Alexander Bob, Rahnfelsstrasse 9A, D-68163 Mannheim; Konstantin Bob, Weberstrasse 17, D-69469 Weinheim, all of Germany

[21] Appl. No.: 284,568
[22] PCT Filed: Dec. 15, 1993
[86] PCT No.: PCT/EP93/03570
  § 371 Date: Jan. 3, 1995
  § 102(e) Date: Jan. 3, 1995
[87] PCT Pub. No.: WO94/13188
  PCT Pub. Date: Jun. 23, 1994

[30] Foreign Application Priority Data

Dec. 15, 1992 [DE] Germany ............ 42 42 291.4

[51] Int. Cl.⁶ ........................................ A61B 1/00
[52] U.S. Cl. ............... 600/114; 604/271; 604/96
[58] Field of Search ............... 600/114, 115, 600/146, 102; 604/271, 96, 172

[56] References Cited

U.S. PATENT DOCUMENTS

| | | | |
|---|---|---|---|
| 3,669,099 | 6/1972 | Silverman | 604/280 |
| 4,321,915 | 3/1982 | Leighton et al. | 600/114 |
| 4,526,175 | 7/1985 | Chin et al. | 604/271 |
| 4,692,154 | 9/1987 | Singery et al. | 604/172 |
| 5,163,927 | 11/1992 | Woker et al. | 604/96 |
| 5,236,423 | 8/1993 | Mix et al. | 600/115 |
| 5,259,364 | 11/1993 | Bob et al. | 600/115 |
| 5,389,100 | 2/1995 | Bacich et al. | 604/271 |

Primary Examiner—Richard J. Apley
Assistant Examiner—John P. Leubecker
Attorney, Agent, or Firm—William W. Jones

[57] ABSTRACT

An apparatus for moving an endoscope along a canal-shaped cavity includes an endoscope having a movable distal end for entry into the cavity and a stationary operating end which remains outside of the cavity. A first portion of the endoscope is contained in a turnout tube which has a turnout area for entry into the cavity, and which also has a fixed end which remains outside of the cavity. A second portion of the endoscope extends from the fixed end of the turnout tube to the operating end of the endoscope. A first drive assembly is operable to move the endoscope and the turnout tube in unison, and a second drive assembly is operable to move the endoscope independently of the turnout tube. A lubricant may be applied through the fixed end of the turnout tube to the portions of the endoscope which are disposed within the turnout tube. Portions of the turnout tube and endoscope are disposed in a bend so as to allow the operating end of the endoscope to remain stationary while at the same time allowing the distal end of the endoscope and the turnout area of the turnout tube to be advanced and/or retracted into and out of the cavity.

13 Claims, 5 Drawing Sheets

METHOD AND APPARATUS FOR MOVING AN ENDOSCOPE ALONG A CANAL-SHAPED CAVITY

TECHNICAL FIELD BACKGROUND ART

The present invention relates to a method for moving an endoscope along a canal-shaped cavity.

Endoscopes have become an important aid in technology and medicine for inspecting canal-shaped cavities that are otherwise inaccessible or only accessible with considerable intervention. Endoscopes are equipped at the distal end with illuminating means and with an optical system for visually detecting the area of the cavity located therebefore. The optical information detected at the distal end of the endoscope is normally either transmitted through the endoscope to the proximal operating end by means of fiber optics, or detected at the distal end by means of a camera chip, guided through an electric wire to the proximal end of the endoscope and made visible on a monitor. Endoscopes customarily have an overall elongate, flexible-rod shape, disregarding the proximal operating end.

To permit inspection of a canal-shaped cavity the endoscope is introduced into the cavity through an access opening. The endoscope is customarily moved further inside by an operating person acting with his hand on the part of the endoscope protruding out of the access opening and from there gradually pushing the endoscope, which is rigid when pushed, ever further into the cavity.

It is relatively troublesome to move the endoscope increasingly into the canal-shaped cavity. It is particularly difficult to advance the endoscope when the canal-shaped cavity to be inspected has narrow bends, strictures or the like. When the canal-shaped cavity has an unsmooth wall consisting of a rather unsolid material there is a danger of the distal end getting stuck on the cavity wall during its advance; this can cause damage to the cavity wall. Particularly when the cavity has several bends the push from the posterior end of the endoscope exerts considerable pressure from the inside against the wall areas located on the outside of the bend. This complicates the further advance of the endoscope.

DISCLOSURE OF THE INVENTION

The invention is based on the problem of providing a less complicated way of moving the endoscope along the cavity with less danger of damaging the cavity wall.

To solve this problem the method according to the invention is characterized in that (a) a turnout tube is used whose outer area is stationary relative to the cavity wall while the endoscope is moved along the cavity and whose inner area receives a partial length of the endoscope;

(b) and anterior parts of the endoscope and of the inner turnout tube area which are located within the cavity are moved forward at least during part of the time in such a way that the rate of motion of the anterior part of the endoscope is substantially half as great as the rate of motion of the anterior part of the inner turnout tube area.

In the inventive method not only the endoscope is introduced into the canal-shaped cavity and advanced along it, but the turnout tube is also introduced between the cavity wall and the endoscope. The turnout tube provides a lining of the cavity which facilitates motion of the endoscope along the cavity and decisively reduces the danger of damage to the cavity wall.

Jointly advancing the anterior part of the endoscope and the anterior part of the inner turnout tube area normally causes these two anterior parts to advance at virtually the same rate. Since one half of a given advanced length of the inner turnout tube area is "used up" for the outer turnout tube area after the turnout area is passed, the anterior part of the endoscope would consequently protrude forward beyond the turnout area of the turnout tube by this half length. To avoid this, the anterior part of the endoscope is moved forward according to the invention at a rate that is substantially half as great as the rate of motion of the anterior part of the inner turnout tube area. This involves a sliding motion of the inner turnout tube area relative to the endoscope.

A preferred, specific possibility for obtaining the stated speed ratio is to exert forward driving force on the anterior part of the endoscope and the anterior part of the inner turnout tube area and simultaneously to exert backward motion determining force on a posterior part of the endoscope extending out of the back of the turnout tube.

The inventive motion sequence of the anterior parts of the endoscope and of the inner turnout tube area can fundamentally be performed continuously for the entire forward motion path. However one can also divide the total motion path into several moving steps taking place successively at time intervals.

The invention allows for the possibility of shifting the endoscope relative to the inner turnout tube area at times when no forward motion of the anterior parts of endoscope and turnout tube is taking place with the described speed ratio, i.e. simply moving it along the cavity within the created lining. A typical situation is for example when the operating person sees that a rather straight cavity portion with a fairly smooth wall is located before the distal end of the endoscope. The operating person can then advance the endoscope a fair distance relative to the altogether stationary turnout tube and thereby inspect this cavity portion. A further example is to extract the endoscope partly or wholly while the turnout tube is altogether stationary; one can then move the turnout tube out of the cavity by pulling on its inner area.

In a preferred development of the invention one can provide the possibility of pressurizing the space between the outer and inner turnout tube areas by means of a fluid. Suitable fluids are liquids or gases. This pressurization causes the outer area and the inner area of the turnout tube to be moved apart or kept apart, the result being minimized friction between these two areas. The inner turnout tube area is kept tight in the longitudinal direction. There is also an advancing effect on the inner turnout tube area because the overpressure prevailing within the stated space strives to move the turnout area of the turnout tube forward. Finally this overpressure can make the inner turnout tube area press against the endoscope over a great length, resulting in a pulling advancing effect on the endoscope. Obviously the space between the outer area and the inner area of the turnout tube must be closed off at a point spaced away from the turnout area to permit the described pressurization to come about.

It is also possible to let the fluid flow or be sucked out of the space between the outer area and the inner area of the turnout tube, whereupon this space flattens out under the effect of the external air pressure, i.e. the inner turnout tube area gets free of the endoscope. This is favorable particularly for moving the endoscope relative to the altogether stationary turnout tube.

A lubricant is preferably located within the space between the endoscope and the inner turnout tube area so as to reduce the friction between these two elements during their relative motions. One can press further lubricant into this space continuously or repeatedly.

The invention also relates to an apparatus for moving an endoscope along a canal-shaped cavity, characterized by:

(a) a turnout tube having, upon use of the apparatus, an outer area which is stationary relative to the cavity wall and an inner area receiving a partial length of the endoscope;

(b) driving means for moving forward in power-operated fashion anterior parts of the endoscope and of the inner turnout tube area which are located within the cavity;

(c) and motion determining means acting on the endoscope for determining the rate of forward motion of the anterior part of the endoscope in such a way that it is substantially half as great as the rate of the anterior part of the inner turnout tube area during operation of the driving means.

This inventive design of the apparatus results in effects and advantages as have been described above in connection with the inventive method.

When beginning to advance the endoscope and the turnout tube into the cavity and during the further course of motion inside one can provide a reserve length of turnout tube and endoscope in a straight position. Particularly when a considerable length of the endoscope is to be introduced, however, it is frequently preferred for reasons of space if part of the turnout tube and—an enclosed—part of the endoscope are provided in a meandering portion as a reserve to be reduced as the anterior part of the endoscope is moved forward along the cavity, a posterior part of the endoscope extending out of the back of the turnout tube reserve portion, and the motion determining means acting on the posterior part of the endoscope. A reserve tightening element can be provided for exerting a counterforce against a straightening of the reserve.

It should be emphasized at this point that the motion determining means particularly tend to have the function of restrainingly reducing the rate of forward motion of the endoscope to the desired rate, or particularly tend to have the function of driving the endoscope in the backward direction relative to the posterior end of the turnout tube, depending on the structure of the apparatus. The motion determining means are preferably intended to impart a predetermined, definite rate to the endoscope so as to obtain the above-described speed ratio between the endoscope and the inner turnout tube area.

The driving means preferably have pressure means for creating frictional engagement with a longitudinal portion of the inner turnout tube area. This normally involves the longitudinal portion being pressed against the endoscope so that forward motive force is also transmitted there. A particularly elegant technical embodiment of the pressure means is to provide a pressure tubing portion disposed in a sheath and surrounding the longitudinal portion of the inner turnout tube area and to pressurize the closed space between the sheath and the pressure tubing portion with a fluid. The inner surface of the pressure tubing portion can be designed so as to favor frictional engagement with the turnout tube, e.g. have a selectively roughened design, be provided with a friction lining, consist of a material with a higher coefficient of friction, etc. When operated the thus formed pressure means at the same time seal off the space between the inner and outer areas of the turnout tube from the surroundings at this point.

In a preferred embodiment of the invention the driving means have an electric motor working—directly or indirectly—on the longitudinal pressure portion of turnout tube and endoscope.

A way of designing the motion determining means that is preferred as being particularly simple is to provide a pair of driving wheels drivable by an electric motor that work on the endoscope.

One can also provide driving means for moving the endoscope relative to the stationary inner turnout tube area. These driving means can particularly likewise be formed by the pair of driving wheels drivable by an electric motor that work on the endoscope. For this purpose these driving wheels can be optionally drivable in either direction of rotation.

One can provide pressure fluid supply means for supplying pressure fluid to the space between the outer and inner areas of the turnout tube. One also preferably provides lubricant press-in means for pressing lubricant into the space between the endoscope and the inner turnout tube area. The advantages involved in pressure fluid supply means and lubricant press-in means were already dealt with above.

It is possible to turn out the turnout tube to form outer and inner areas not only at the front but additionally in the posterior area, which is located outside the canal-shaped cavity during operation of the apparatus. When the endoscope is moved into the cavity the outer, stationary area of the turnout tube becomes ever longer at the anterior end and the outer, stationary area of the turnout tube ever shorter at the posterior end. This design of the inventive apparatus offers advantages with respect to the necessary length of the endoscope, as will become clearer below in the description of embodiment examples.

To reduce friction the turnout tube can be coated with a low-friction material, e.g. polytetrafluoroethylene, on the outside (and thus also on the inside in the turned out, outer area) and/or on the inside.

To move the endoscope backward a first possibility is simply to withdraw the endoscope within the stationary, inner turnout tube area and then take the turnout tube out of the cavity by pulling on its inner area. A second possibility is to proceed conversely as with forward motion, i.e. to move the endoscope backward at substantially half the rate of the inner turnout tube area. The motion determining means then exert—in the reverse direction as with forward motion—a force on the endoscope that ensures the described speed ratio. This manner of backward motion has the advantage that the canal-shaped cavity can be inspected a second time.

A further object of the invention is a method for moving an endoscope along a canal-shaped cavity, characterized in that a) a turnout tube is used whose outer area is stationary relative to the cavity wall when the endoscope is moved along the cavity and whose inner area receives a partial length of the endoscope;

b) the endoscope is moved in a sequence of moving steps in a first direction and an opposite second direction, c) the endoscope being moved jointly with the inner turnout tube area during the moving steps in the first direction, d) and the endoscope being moved relative to the inner turnout tube area during the moving steps in the second direction;

e) the moving steps in the first direction resulting altogether in a greater length than the moving steps in the second direction.

In this variant of the invention the endoscope is moved jointly with the inner turnout tube area during the moving steps in the first direction. The moving steps in the opposite second direction are performed by the endoscope without concomitant motion of the turnout tube, so that the turnout area of the turnout tube does not stay behind relative to the endoscope.

It is most useful to make the moving steps in the second direction half as great as the moving steps in the first direction, so that the endoscope and the turnout tube are jointly moved ever further into the cavity as a result. If the moving steps of the endoscope in the second direction are smaller than one half of the moving steps in the first direction, the distal end of the endoscope will come ever further forward beyond the turnout area of the turnout tube in the course of time. If the moving steps of the endoscope in the second direction are greater than half of the moving steps in the first direction, the distal end of the endoscope will stay back increasingly relative to the turnout area of the turnout tube.

It is most practical to perform the moving steps in the first direction alternatingly with the moving steps in the second direction. However it is also possible—to mention only one example—to perform two successive moving steps in the first direction, then one moving step in the second direction, etc.

When the endoscope is moved ever further into the cavity the first direction is the direction of inward motion and the second direction is the direction of outward motion. When the endoscope is moved backward ever further out of the cavity the first direction is the direction of outward motion and the second direction is the direction of inward motion. It is emphasized that the inventive method for moving the endoscope can be used for moving it into the cavity and/or out of the cavity.

The inventive method is particularly suitable for performing the described moving steps not by manual action on the endoscope and the turnout tube but by outside force. There are a great number of technical possibilities for doing this, e.g. electric motors, cylinder-piston units and the like. The embodiment example described below shows one specific possibility in detail. The motion of the endoscope along the canal-shaped cavity can take place quasi-automatically but under the operating person's control.

It is particularly simple to move the endoscope and the inner turnout tube area in the first direction if these two elements are moved as one unit. For this purpose one can couple the inner turnout tube area and the endoscope with each other for the moving steps in the first direction.

A further object of the invention is an apparatus for moving an endoscope along a canal-shaped cavity, characterized by:

a) a turnout tube having, upon use of the apparatus, an outer area which is stationary relative to the cavity and an inner area receiving a partial length of the endoscope;

b) first driving means for moving the endoscope and the inner turnout tube area at substantially the same rate in power-operated fashion and step by step in a first direction; and c) second driving means for moving the endoscope in power-operated fashion and step by step in a second direction opposite the first direction.

The invention can be used, on the one hand, for inspection and for performing tasks in technical plants and facilities. Some examples among many are nuclear reactors, chemical plants, pipeline systems. On the other hand, the invention can be used favorably in the field of medicine, particularly for exploring cavities or tubular canals in the body. Endoscopes have become widely used particularly for exploring the esophagus, the stomach, the duodenum from the stomach, the intestine from the anus, the urethra, the bladder and the ureters. Endoscopes permit the use of minimally invasive surgical techniques today. Endoscopes generally have a so-called working channel through which diverse working elements can be introduced and operated, e.g. small forceps for removing tissue specimens, biopsy needles, heatable cutting wires, small scissors, coagulation electrodes or the like. Finally they generally have a fluid channel for rinsing fluid and operating wires for bending the distal end of the endoscope in several directions. Altogether the term "endoscope" in the present application includes all types of instruments or devices to be moved along a canal-shaped cavity, even when optical inspection is not the primary purpose or does not take place at all.

The invention also provides the possibility of first moving an endoscope to a certain point of a canal-shaped cavity with a visual check, withdrawing the endoscope from the lining turnout tube and then advancing a different instrument for performing a certain task through the lining turnout tube quite unproblematically to that point where something is to be done. An example is a balloon dilatation instrument.

An especially troublesome, difficult and time-consuming task up to now was coloscopy, i.e. exploration of the large intestine from the anus. The intestine has bends and frequently strictures. Up to now coloscopic examinations have accordingly been elaborate and unpleasant for the patient and therefore hardly suitable for a broad application, particularly in the sense of regular medical check-ups. A coloscope can only be handled properly if the physician and assistant staff have special experience.

This situation is particularly adverse because anomalies in the intestinal wall, for example polyps, adenomas and carcinomas, are becoming increasingly frequent in many regions of the world and because early detection greatly raises the chances of recovery for the patient in question or leads to a considerable prolongation of his life.

It is thus extremely desirable to have an endoscope that is movable along the intestine with less complication and less risk and that can also be used by physicians with less relevant experience.

Up to now the patient's position had to be repeatedly changed during a coloscopy and one had to press selectively on his abdomen to attempt to straighten the intestinal bends far enough for the endoscope to be advanced properly. The invention attains a crucial improvement in the medical field particularly for coloscopy because the lining of the intestine with the protective, smooth-guiding, outer area of the turnout tube substantially reduces the danger of the sensitive intestinal wall being damaged or even perforated. The invention makes total coloscopy as far as the transition from the large intestine to the small intestine accessible for a genuinely broad application, for example general medical check-ups at suitable time intervals as of a certain age. It results in a saving of staff for the examinations.

BRIEF DESCRIPTION OF THE DRAWINGS

The invention and developments of the invention will be explained in more detail in the following with reference to an embodiment example shown in partly schematic fashion.

DETAILED DESCRIPTION OF SPECIFIC EMBODIMENTS OF THE INVENTION

Figure 1:
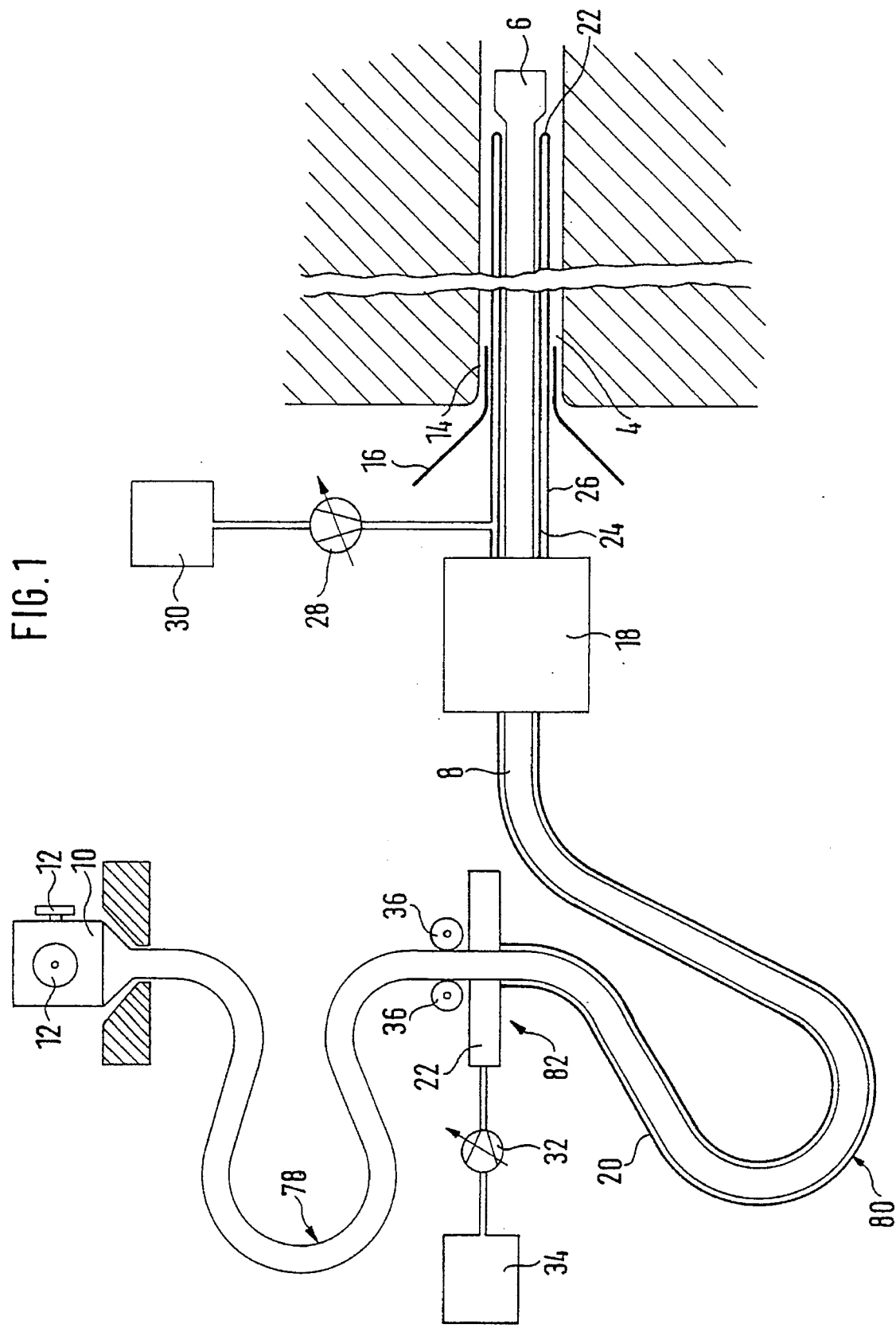
FIG. 1 shows in schematic form an apparatus for moving an endoscope along the intestine.

FIG. 1 shows the apparatus in a state in which endoscope 2 has already been moved a distance into intestine 4 of a patient. Endoscope 2 comprises substantially distal end 6, endoscope shaft 8 and operating end 10. Endoscope shaft 8 is about 3200 mm long and has a diameter of 9 to 13.5 mm. Distal end 6 has a somewhat greater diameter. Rotatable operating disks 12 for operating wires to bend distal end 6 are schematically shown at the operating end. Tube 16 is introduced into anus 14 to prevent the patient from closing the anal sphincter muscle.

At a distance of about 10 to 20 cm from anus 14 there are first driving means 18 to be described more exactly below with reference to FIG. 2. Turnout tube 20 is attached with its posterior end to platelike part 22 and surrounds endoscope shaft 8 from here to near the anterior end of endoscope 2. Near the anterior end of endoscope 2 turnout tube 20 is turned out 180° and then back again and leads from there back to first driving means 18. The anterior end of turnout tube 20 is referred to as turnout area 22. Turnout tube 20 thus has inner area 24 and outer area 26 between turnout area 22 and the first driving means 18.

The space between inner area 24 and outer area 26, closed on the right in FIG. 1 by turnout area 22 and closed intermittently on the left in FIG. 1 within first driving means 18, can be subjected to liquid pressure by means of pump 28. Pump 28 sucks the liquid from supply vessel 30. The liquid used can be water with an added wetting agent.

Between first driving means 18 and plate 23 endoscope shaft 8 with surrounding tube 20 assumes a meandering path forming a first flexure or bend 80. In the area of plate 23 lubricant can be pressed into the space between endoscope shaft 8 and tube 20, as described more exactly below with reference to FIG. 3. FIG. 1 shows lubricant pump 32 and associated supply vessel 34 for lubricant. The lubricant may be vegetable oil for example.

On the side of plate 23 facing away from tube 20 there are a pair of driving wheels 36 whose trough-shaped outer peripheries are in frictional engagement with endoscope shaft 8 from two sides. Driving wheels 36 form second driving means 72 together with an electric motor not shown.

Endoscope shaft 8 assumes a meandering path forming a second flexure or bend 78 between driving wheels 36 and operating end 10 of endoscope 2.

Figure 2:
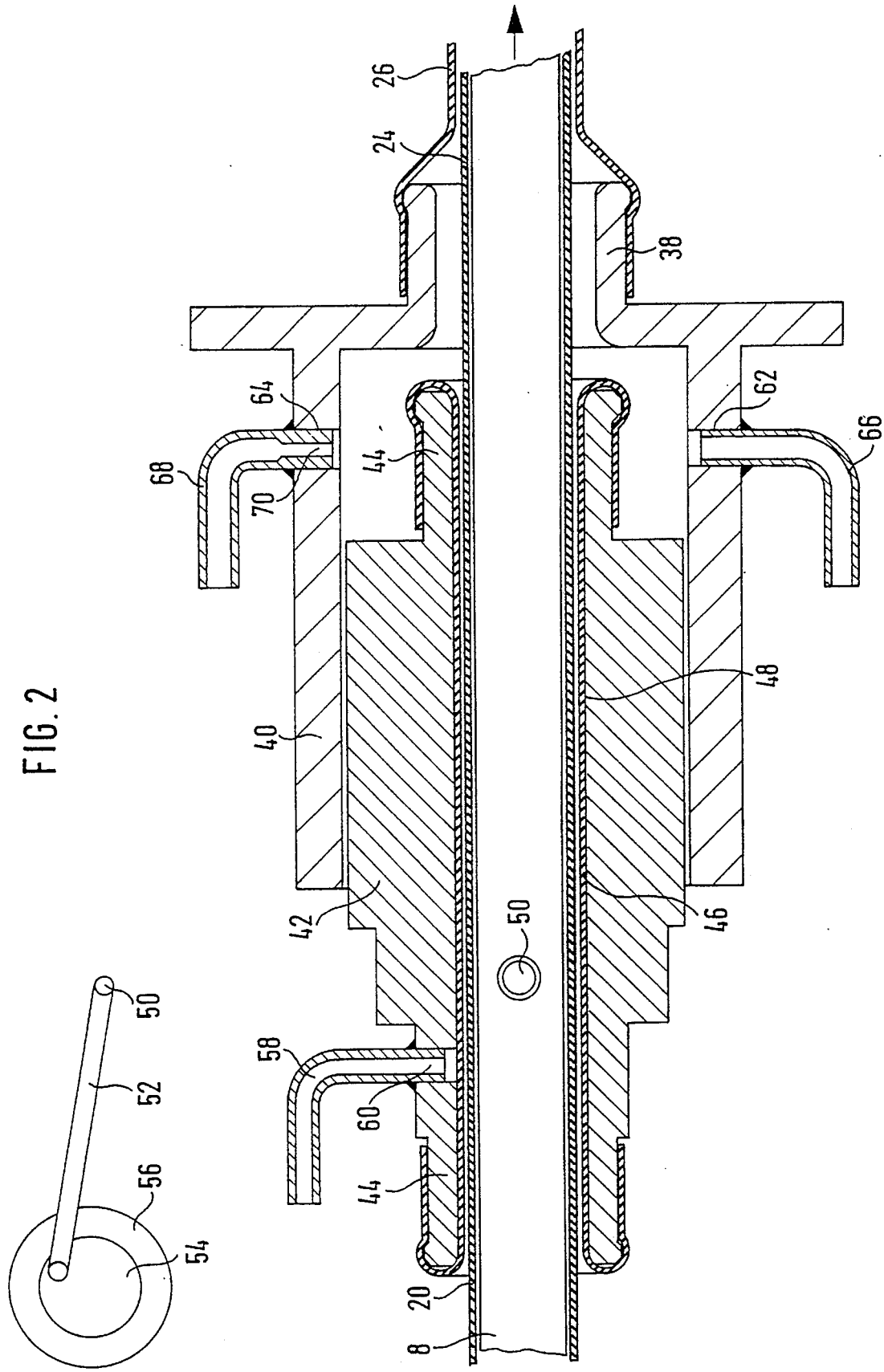
FIG. 2 shows first driving means of the apparatus of FIG. 1 in longitudinal section and on a larger scale.

In FIG. 2 one can see endoscope shaft 8 and turnout tube 20. On the right in FIG. 2 one sees inner area 24 and outer area 26 of turnout tube 20. The end of outer area 26 is attached to a rightward pointing tube socket 38 on cylinder 40.

Cylinder 40 contains piston-shaped sheath 42 which is guided movably in the axial direction with its outer periphery within the bore of cylinder 40. The two axial ends of sheath 42 are formed as tube sockets 44. Tubing portion 46 extends longitudinally within inside through bore 48 in sheath 42 and is turned out at its two ends and attached tightly to tube sockets 44. Endoscope shaft 8 with surrounding tube 20 being in one layer there is guided through inside bore 48 in sheath 42 within tubing portion 46. The wall thickness of tube 20 is 0.6 to 1.5 mm. The diameters of the components disposed within inside bore 48 are selected so that there is some play between tubing portion 46 and tube 20 and between tube 20 and endoscope shaft 8.

Sheath 42 has a pair of pins 50 protruding diametrically away from the outer periphery. On the top left in FIG. 2 one can see how pins 50 are connected via rods 52 with eccentric disk 54 which is drivable to rotate by electric motor 56. Sheath 42 can in this way be driven in pendulum fashion in its axial direction. The total stroke of this axial motion is 30 mm in the present embodiment example. One can also use only one pin 50 and one connecting rod 52.

The apparatus will now be described first with a mode of functioning in which endoscope shaft 8 and tube 20 are alternatingly moved as one unit in a first direction and endoscope shaft 8 is moved alone in an opposite second direction; this corresponds to the variant of the invention described second in the introduction to the description. An alternative mode of functioning will then be described below in which the anterior part of endoscope 2 is moved at about half the rate of inner area 24 of tube 20; this corresponds to the variant of the invention described first in the introduction to the description.

The space between tubing portion 46 and inside bore 48 in sheath 42 can be subjected to positive fluid pressure via connection piece 58 and through radial bore 60 in sheath 42. When this space is positively pressurized, the tubing portion 46 moves radially inward and presses tube 20 against the outer periphery of endoscope shaft 8 over the length of sheath 42. Negative pressure can also be produced optionally in the space between tubing portion 46 and inside bore 48 via connection piece 58 and bore 60 to draw tubing portion 46 radially outward against inside bore 48 again, thereby unblocking tube 20 and endoscope shaft 8. The application of positive pressure and the application of negative pressure in the space between tubing portion 46 and inside bore 48 are controlled so that the stated space is under positive pressure substantially for the time phase in which sheath 42 is moved from the left to the right, and under negative pressure for the time phase in which sheath 42 is moved from the right to the left. Sheath 42 thus carries along the unit comprising endoscope shaft 8 and tube 20 to the right in its motion from the left to the right. When sheath 42 moves from the right to the left, on the other hand, the unit comprising endoscope shaft 8 and tube 20 is not carried along. Instead of applying negative pressure as described, one can more simply release the positive pressure used for clamping.

Where tube socket 44 is located on the right end of sheath 42 there is a free space 41 between sheath 42 and inside bore in cylinder 40. Lower radial bore 62 and upper radial bore 64 open into this space 41, with connection piece 66 being seated in lower bore 62 and connection piece 68 in upper bore 64. Connection piece 68 has throttling port 70. Pump 28 shown in FIG. 1 is connected to piece 66 (the connection between pump 28 and turnout tube 20 being shown there for reasons of greater clarity to the right of first driving means 18). Through connection piece 66 the free space of cylinder 40 can be subjected to fluid pressure. During pressurization the pressure in this space is regulated to about 0.7 bars.

Through connection piece 68 the fluid can flow depressurized back into supply vessel 30. FIG. 2 shows clearly that the stated interior space of cylinder 40 communicates with the space between outer area 26 and inner area 24 of turnout tube 20 so that the stated fluid pressure likewise prevails there during pressurization.

However the stated space within cylinder 40 and thus also the space between outer area 26 and inner area 24 of turnout tube 20 is not subjected to fluid pressure permanently. By suitably regulating pump 28 or regulating the return flow to supply vessel 30 one instead ensures that the pressure drops to about 0.2 bars during certain time phases. The time sequence is controlled as follows.

When sheath 42 is located in its position on the very left, tube 20 is pressed against endoscope shaft 8—as described above—and the stated space in cylinder 40 thus also sealed off on the left. Subsequently the space 4/, and thus the space between outer area 26 and inner area 24 of turnout tube 20 is pressurized in the described way. At about the time when sheath 42 has reached its end position on the right by means of the rods 52 the pressure between outer area 26 and inner area 24 of turnout tube 20 is reduced, as described, and the pressure of tube 20 against endoscope shaft 8 is lifted, as described. Sheath 42 can consequently then be moved back to the left by means of the rods 52 without moving the tube 20 and endoscope shaft 8 to the left.

Figure 3:
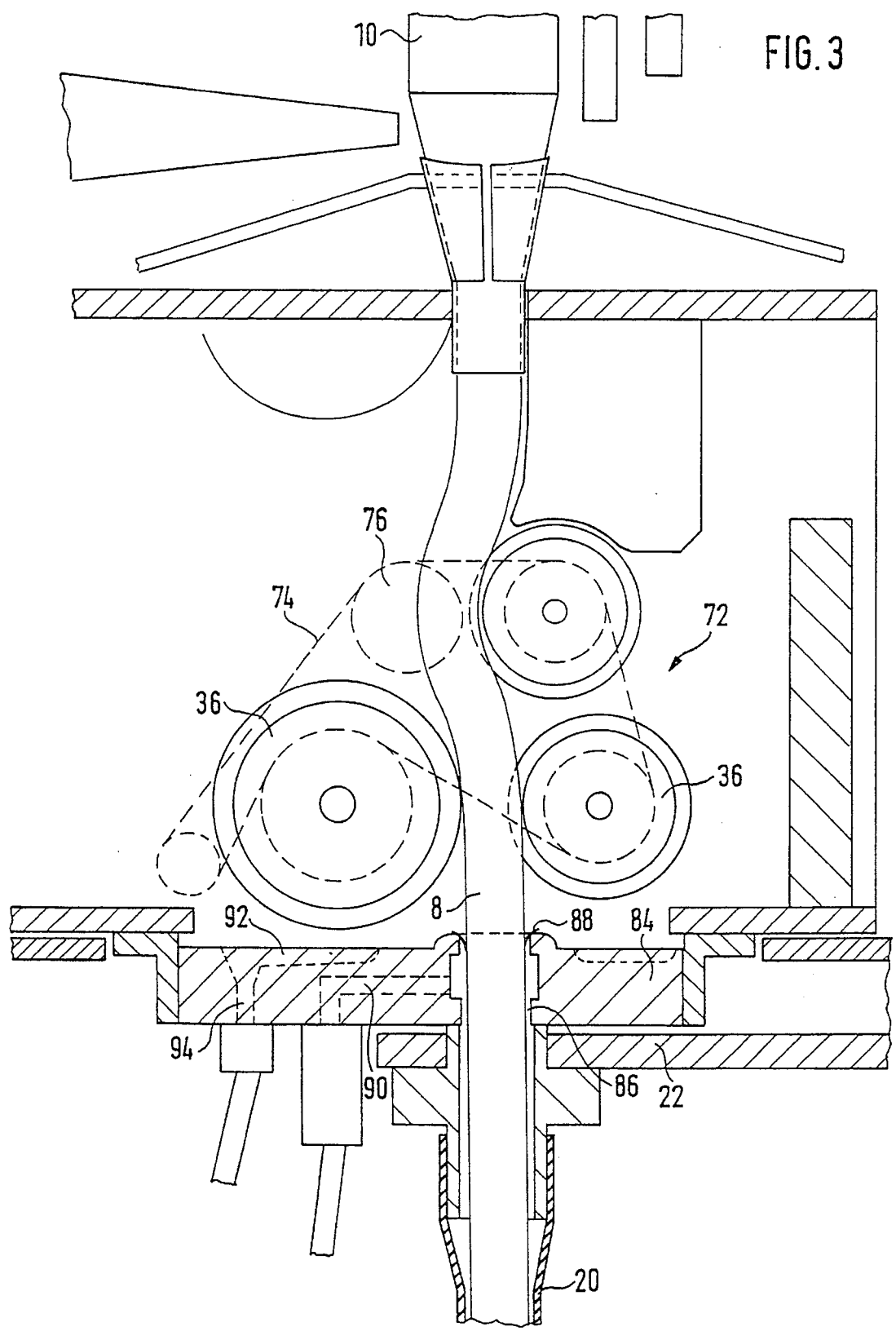
FIG. 3 shows a partial section of second driving means and lubricant press-in means of the apparatus of FIG. 1.

FIG. 3 illustrates second driving means 72 whose driving wheels 36 were already described in connection with FIG. 1. Driving wheels 36 are connected via chain 74 with driving chain wheel 76 which is in turn drivable in both directions of rotation by an electric motor (not shown). During the time phase in which tube 20 is not pressed against endoscope shaft 8 by means of tubing portion 46 and sheath 42 performs its free motion from the right to the left—the second driving means 72 draw endoscope shaft 15 mm upward, i.e. backward. Endoscope shaft 8 can perform this retracting motion without carrying along tube 20 because tube 20 is not pressed against endoscope shaft 8 anywhere with considerable contact pressure. These retracting motions of endoscope shaft 8 increase the bend 78 (see FIG. 1) between second driving means 36 and the operating end 10 of the endoscope. During the above-described advancing motion of endoscope shaft 8 together with inner area 24 of turnout tube 20, the bend 80 between first driving means 18 and plate 23 becomes smaller. At the end of the advancing motion of endoscope 2 into intestine 4 the bend 80 is virtually used up; there are typically about 1500 mm of endoscope length in intestine 4 and about 1500 mm of endoscope length in bend 78.

In FIG. 3 one can see further details of the lubricant press-in means 82. Platelike lubricant supply member 84 is disposed above plate 23. Component 84 has through opening 86 with endoscope shaft 8 guided there-through. In its upper area through opening 86 is sealed off from endoscope shaft 8 by means of lip seal 88. In the area located thereunder through opening 86 has a clearly greater inside diameter than the outside diameter of endoscope shaft 8. Supply channel 90 for the lubricant opens there, being connected to lubricant pump 32. On its top side lubricant supply means 84 is provided with a circumferential depression 92 and a lubricant return channel 94 for any lubricant flowing upward between the seal 88 and the endoscope shaft 8 the return channel 94 leads back to vessel 34.

Lubricant passing through the supply channel 90 under pressure into the area between through opening 86 and endoscope shaft 8 spreads over the entire length between inner area 24 of turnout tube 20 and endoscope shaft 8. Surplus amounts of lubricant can escape into intestine 4 in the vicinity of the turnout area 22 of turnout tube 20. Lubricant press-in means 82 can be controlled so that a short shot of lubricant is released at the beginning of each retracting motion of the endoscope shaft 8 caused by the driving wheels 36.

Second driving means 72 can be used not only to perform the described 15 mm retracting steps but also to optionally advance or retract endoscope shaft 8 over a longer path. A typical application for this motion is when distal end 6 of endoscope 2 has passed the innermost bend of the large intestine. This is followed by a relatively straight portion of large intestine which one can explore by advancing the endoscope without advancing the inner area 24 of turnout tube 20. There are endoscopes whose distal end can be bent up to 160° with the described wire pulls, and with the distal end 6 advanced beyond the turnout area 22 one can thus also explore the intestine quasi looking backward.

It is noted that the above-described sequences of positive pressurization, pressure relief, application of negative pressure and motion of endoscope shaft 8, along with inner area 24 of turnout tube 20, and without inner area 24 of turnout tube 20 take place in exactly the reverse order when one retracts the endoscope 2 and turnout tube 20 from the intestine 4 step wise. One can then re-examine the intestine 4 while retracting the endoscope 2 out of the intestine. Obviously one must advance rather than withdraw intermittently by 15 mm during this retracting motion with the second driving means 72.

Turnout tube 20 can be made of silicone and be coated on both sides with polytetrafluoroethylene for example.

Cylinder 40 can be attached along with sheath 42 to the apparatus so as to pivot about a vertical axis so that the alignment of endoscope shaft 8 emerging from cylinder 40 on the patient side can be adjusted relative to the patient. The entire apparatus can also be vertically adjustable so that the level of endoscope shaft 8 emerging from cylinder 40 can be adapted to the level of the anus of the patient positioned for examination. Obviously the patient's position relative to the apparatus should be maintained in the course of the examination; in particular the distance between anus 14 and first driving means 18 should be constant.

The described apparatus also has the advantage for the examining physician that he can work with operating end 10 of endoscope 2, said operating end 10 being stationary on the apparatus. Motion of endoscope shaft 8 inward and outward has no influence on the stationary position of operating end 10. The physician can conveniently control the motion of the endoscope shaft inward and outward by electric switches on the apparatus. Before bends of the intestine he bends distal end 6 of endoscope 2 so that it points substantially in the direction of the course of the intestine located before distal end 6. Alternatively it is e.g. possible to push turnout tube 20 and endoscope shaft 8 gradually ever further into intestine 4 in a state in which the anterior end of distal end 6 is slightly behind (i.e. in FIG. 1 to the left of) turnout area 22. Turnout area 22 then always slightly precedes the anterior end of distal end 6 so that distal end 6 is never in danger of coming in contact with the intestinal wall while being pushed inside.

The preceding description makes it clear that, in the described embodiment example, second driving means 72 at the same time constitute the driving means for moving endoscope shaft 8 a greater distance forward or backward as required, independently of turnout tube 20.

It is pointed out that one can for example also use two driving wheels like driving wheels 36 of second driving means 72 instead of the clamping means described particularly with reference to FIG. 2. For moving back endoscope shaft 8 relative to turnout tube 20 one can for example slightly enlarge the center distance between these two driving wheels, thereby eliminating the clamping effect between turnout tube 20 and endoscope shaft 8.

The above description also makes it apparent that endoscope shaft 8 along with distal end 6 is moved forward and backward, strictly speaking, and not operating end 10.

The other variant of motional functioning of the apparatus will now be described.

In the time phases when first driving means 18 perform a motion of turnout tube 20 and endoscope shaft 8 in the first direction, one can ensure e.g. by second driving means 72 that endoscope shaft 8 is moved in the first direction at half the rate or over half the path compared to sheath 42. In other words, the endoscope shaft performs a lagging sliding motion relative to turnout tube 20 during motions in the first direction. In this case there are strictly speaking no moving steps of endoscope shaft 8 in the second direction. The precondition for this is given, namely that the friction between tubing portion 46 and the outer periphery of turnout tube 20 in first driving means 18 is greater than between endoscope shaft 8 and turnout tube 20. Since bend 80 is gradually used up, endoscope shaft 8 is drawn backward there by driving wheels 36 at the same rate as the anterior part of endoscope shaft 8 moves forward into intestine 4.

One can even go so far as to perform the motion of endoscope shaft 8 and turnout tube 20 in the first direction continuously instead of intermittently. If one e.g. replaces the clamping means or first driving means described particularly with reference to FIG. 2 by a pair of driving wheels frictionally engaged with turnout tube 20 and ensures with further driving means like second driving means 72 that turnout tube 20 or inner area 24 of turnout tube 20 moves in the first direction at twice the rate of endoscope shaft 8, one likewise attains the goal of moving forward turnout tube 20 and endoscope shaft 8 fitting together in intestine 4.

Figure 4:
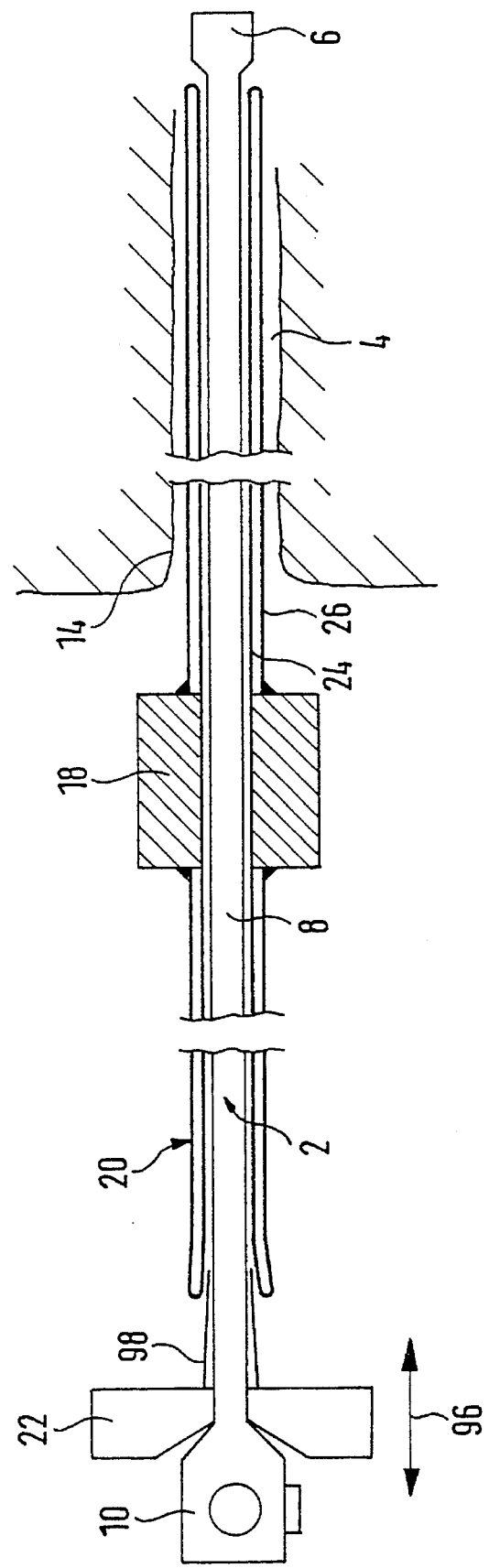
FIG. 4 shows in schematic form as in FIG. 1 a further embodiment of an apparatus for moving an endoscope along the intestine.

The embodiment of FIG. 4 differs from the above-described embodiment of FIGS. 1 to 3 essentially in that turnout tube 20 is turned out in its area to the left of first driving means 18 and attached with that end to first driving means 18. Between first driving means 18 and plate 23 endoscope shaft 8 along with turnout tube 20 has a straight course instead of bend 80. Operating end 10 of endoscope 2 is seated directly on plate 23. Plate 22 is movable in the longitudinal direction of endoscope shaft 8, see arrow 96. An example of this is to mount plate 22 on a slide movable in the horizontal direction, with second driving means (not shown) being provided for driving plate 23 to the left at least in FIG. 4.

When endoscope shaft 8 is moved into intestine 4 the portion of turnout tube 20 located to the left of first driving means 18 is shortened, just as the portion of turnout tube 20 located to the right of first driving means 18 is lengthened. In other words, inner area 24 of turnout tube 20 is moved through first driving means 18 step by step. The motions of endoscope shaft 8 in the second direction are produced by driven motions of plate 23 to the left in FIG. 4. It is of course also possible to construct the embodiment of FIG. 4 so that the motions in the first direction and/or in the second direction are performed continuously, as described above in connection with the first embodiment.

In FIG. 4 one can also see annular apronlike part 98 which is attached, pointing to the right, to plate 23 and protrudes into the space between inner area 24 of turnout tube 20 and endoscope shaft 8, inner area 24 of turnout tube 20 being in contact with part 98 sealed off as well as possible. Lubricant can be pressed out of the space within apronlike part 98 into the space between inner area 24 of turnout tube 20 and outer surface of endoscope shaft 8, as described in connection with the first embodiment.

The embodiment of FIG. 4 has the advantage over the first embodiment that one can work with a commercial coloscope having a length of a good 1500 mm. At the beginning this endoscope length is located between anus 14 and plate 23. After endoscope shaft 8 has been moved into intestine 4 plate 23 has moved near first driving means 18; the coloscope length is located between first driving means 18 and the exploring end in intestine 4.

The embodiment example of FIG. 4 makes it particularly clear that in embodiments of the apparatus with no reserve of tube 20 and endoscope shaft 8 (reserve 80) a backward restraining force must be exerted on endoscope shaft 8 in the second variant of motional functioning to adjust the rate of motion of the anterior part of endoscope shaft 8 to substantially half the rate of motion of the anterior part of inner area 24 of tube 20. This is done in the embodiment of FIG. 4 by a motion of plate 23 to the right at a corresponding rate. It is thus more suitable to speak of motion determining means rather than second driving means in the second variant of motional functioning.

While it was advantageous in the first variant of motional functioning to apply a high contact pressure between inner area 24 of tube 20 and endoscope shaft 8 by means of tubing portion 48 in sheath 42 and also a considerable contact pressure between inner area 24 of tube 20 and the endoscope shaft further forward in intestine 4 in order to move the anterior part of inner area 24 of tube 20 and the anterior part of endoscope shaft 8 as a unit, it is more favorable in the second variant of motional functioning if these contact pressures tend to be somewhat lower so as not overly to impede the relative sliding motion between faster tube 20 and slower endoscope shaft 8. On the other hand it is favorable in the second variant to ensure a fairly high coefficient of friction between tubing portion 46 and the outer periphery of inner area 24 of tube 20, e.g. by giving tubing portion 46 a roughened inner surface.

Experiments have shown that it is indeed possible exert sufficient advancing force on inner area 24 of tube 20 and to exert advancing force on endoscope shaft 8 by the pulling effect between inner area 24 of tube 20 and endoscope shaft 8, on the one hand, and to exert a backward force on the endoscope shaft by means of motion determining means 72 so that it stays behind inner area 24 of tube 20 with the described speed ratio, on the other hand.

The pressure in the space between outer area 26 and inner area 24 of tube 20 is preferably 0.4 to 1.2 bars, particularly 0.6 to 0.8 bars. The pressure with which tubing portion 46 is pressed inward is preferably 0.8 to 1.6 bars, particularly 1 to 1.3 bars, whereby this pressure should be somewhat higher to ensure the seal there than the pressure between the inner and outer areas of tube 20. The pressure with which lubricant is pressed in is preferably 0.2 to 0.8 bars. All pressure values stated in the application refer to pressure above atmospheric. The wall thickness of tube 20 is preferably 0.8 to 1.2 mm, particularly 0.9 to 1.1 mm.

It is pointed out that the manner of driving sheath 42 in the longitudinal direction described with reference to FIG. 2 is only one of several possibilities. Another, likewise preferred possibility is to provide on sheath 42 a toothed rack extending in the longitudinal direction that meshes with a gearwheel driven by an electric motor. This has the advantage of constant speed over the above-described crank gear. It is readily possible to design sheath 42 for a stroke of up to 25 cm or even more.

Obviously it is useful to coordinate the relation of the rate of motion of sheath 42 and the rate of motion of endoscope shaft 8 defined by motion determining means 72 by a suitable control means so as to obtain the described speed ratio. A suitable control means for this purpose can be produced with the knowledge of the average expert.

Figure 5:
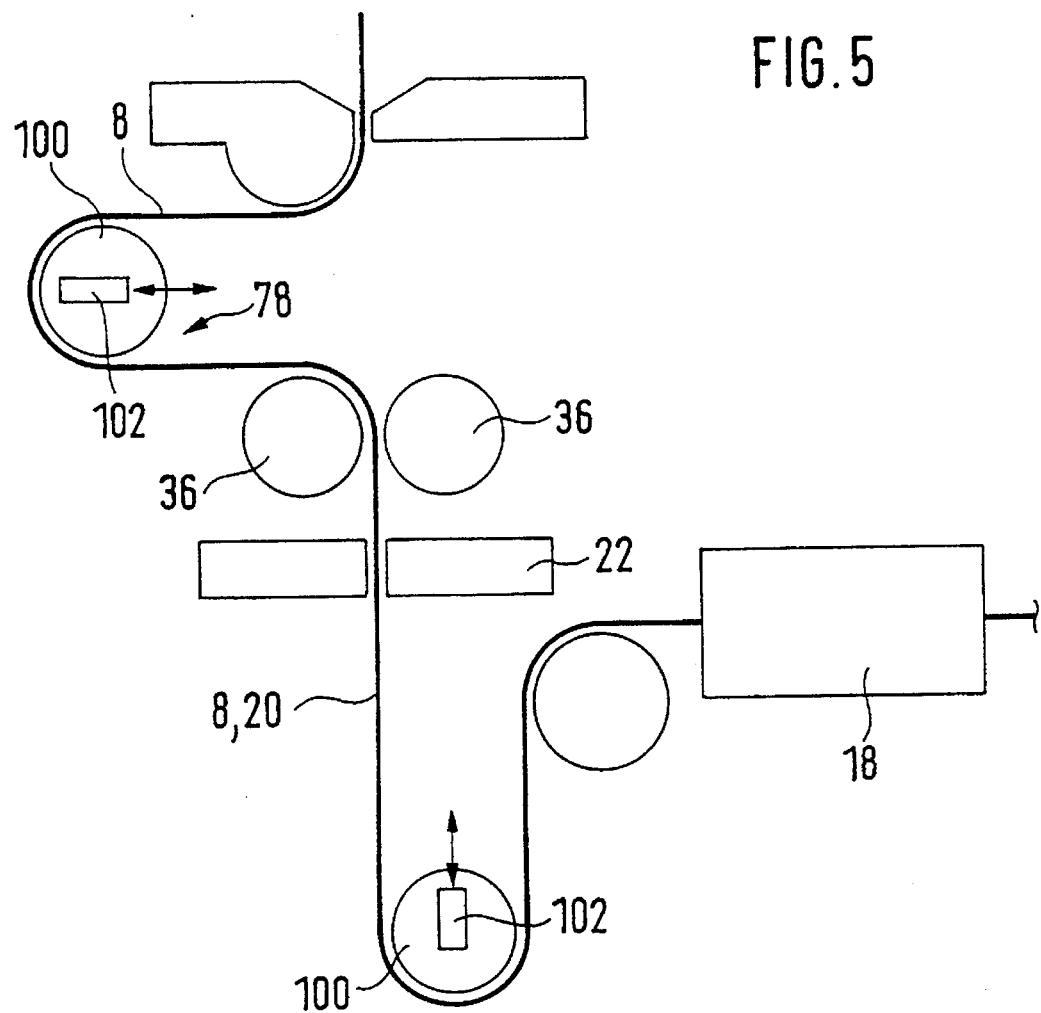
FIG. 5 shows in schematic form as in FIG. 1 a variant with a reserve tightening element.

With reference to FIG. 5 one can see that a bend tightening element in the form of deflection roller 100 can be provided for bulge 80 and for bend 78 in each case. Each of deflection rollers 100 is acted upon by a spring (not shown) in such a way that bend 80 or 78 is kept tight. Schematically shown distance sensor 102 is also provided for each of deflection rollers 100. By comparing the signals from the two distance sensors 102 one can also determine whether distal end 6 of endoscope shaft 8 is located properly somewhat before turnout area 22 of tube 20. If a deviation from the desired relative position is determined one can intervene to correct it, e.g. by slightly increasing or lowering the speed of driving wheels 36.

Figure 6:
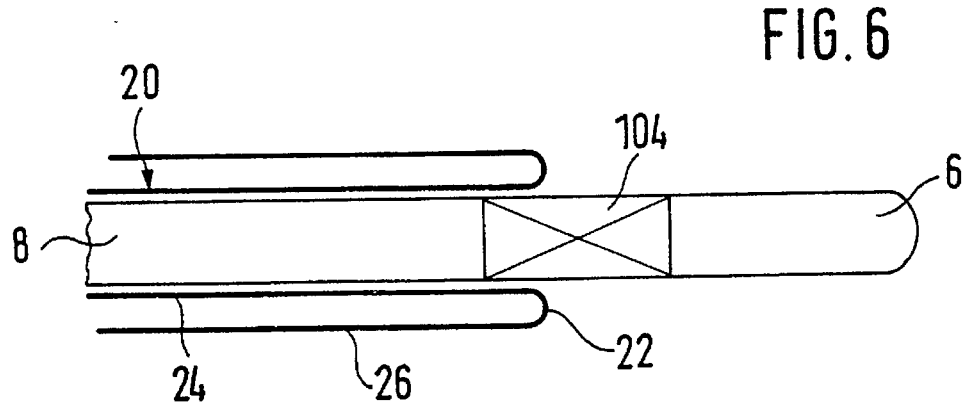
FIG. 6 shows schematically the distal end of the endoscope with a relative position sensor.

With reference to FIG. 6 a more direct determination of the desired position of distal end 6 of endoscope shaft 8 relative to turnout area 22 of tube 20 will be described. Slightly recessed from the anterior end of the endoscope, basically known membrane switch 104 is attached to the outside thereof. When membrane switch 104 is pressurized by inner area 24 of tube 20 and thereby closed, a signal is provided which means that endoscope shaft 8 should not stay back further relative to the forward motion of turnout area 22. On the basis of this signal one can e.g. slightly adjust the rate of the motion determining means so as to make the rate of motion of endoscope shaft 8 somewhat greater than before. It is most advantageous to provide a double switch with two switching points spaced in the longitudinal direction. The desired relative position of distal end 6 is reached when the rear switching point is closed and the front switching point is open.

We claim:

1. A method for moving an endoscope and turnout tube assembly through a canal-shaped cavity, said method comprising the steps of:
   a) moving the turnout tube and endoscope together in the cavity in a manner which would cause a turnout area in the turnout tube to move at a rate which is approximately one half the rate of movement of a distal end of the endoscope; and
   b) simultaneously retarding movement of the endoscope without retarding movement of the turnout tube, so that the distal end of the endoscope actually moves forward at a rate which is less than twice the rate of movement of the turnout area of the turnout tube through the cavity.

2. The method of claim 1 further providing the step of holding an operating end of the endoscope stationary during operation of the assembly.

3. The method of claim 2 further providing the step of providing slack in a portion of the endoscope between its distal end and its stationary end so that the distal end can be moved away from the stationary end without moving the stationary end.

4. The method of claim 2 comprising the further step of injecting a lubricant into an end of said turnout tube which is opposite said turnout area of the turnout tube and which end is fixed during operation of the assembly.

5. An assemblage for examining the interior of a canal-shaped cavity, said assemblage comprising:
   a) an endoscope having a movable distal end for positioning within the cavity, and having an opposite stationary operating end for positioning outside of the cavity;
   b) a turnout tube embracing a portion of the endoscope, said turnout tube having a movable turnout area for positioning within the cavity, and having an opposite fixed end for positioning outside of the cavity;
   c) drive means disposed between said movable distal end and said stationary operating end of said endoscope, said drive means being operable to advance and retract said endoscope in said cavity; and
   d) means for providing slack in said endoscope between said movable distal end and said stationary operating end of said endoscope so as to allow said movable distal end of said endoscope to be moved away from said stationary operating end of said endoscope without moving said operating end of said endoscope.

6. The assemblage of claim 5 wherein said drive means includes a first portion operable to engage said turnout tube and said endoscope.

7. The assemblage of claim 6 wherein said drive means includes a second portion operable to engage only said endoscope.

8. The assemblage of claim 5 wherein said means for providing slack includes a bend in a portion of said endoscope which is embraced by said turnout tube.

9. The assemblage of claim 5 wherein said means for providing slack includes a bend in a portion of the endoscope which is not embraced by said turnout tube.

10. The assemblage of claim 5 further comprising lubrication means adjacent to said fixed end of said turnout tube, said lubrication means being operable to feed a lubricant into said turnout tube via said fixed end thereof.

11. An assemblage for examining the interior of a canal-shaped cavity, said assemblage comprising:
   a) an endoscope having a movable distal end for positioning within the cavity, and having an opposite stationary operating end for positioning outside of the cavity;
   b) a turnout tube embracing a portion of the endoscope, said turnout tube having a movable turnout area for positioning within the cavity, and having an opposite fixed end for positioning outside of the cavity; and
   d) a flexible bend formed in said endoscope between said movable distal end and said stationary operating end of said endoscope so as to allow said movable distal end of said endoscope to be moved away from said stationary operating end of said endoscope without moving said operating end of said endoscope.

12. The assemblage of claim 11 wherein said bend is disposed in a portion of said endoscope which is embraced by said turnout tube.

13. The assemblage of claim 11 wherein said bend is disposed in a portion of said endoscope which is disposed between said fixed end of said turnout tube and said stationary operating end of said endoscope.

\* \* \* \* \*